United States Patent [19]
Badr et al.

[11] Patent Number: 5,830,453
[45] Date of Patent: Nov. 3, 1998

[54] USE OF IL-13 TO INDUCE 15-LIPOXYGENASE

[75] Inventors: Kamal F. Badr, Atlanta; Fadi G. Lakkis, Decatur, both of Ga.

[73] Assignee: Emory University, Atlanta, Ga.

[21] Appl. No.: 445,311

[22] Filed: May 19, 1995

[51] Int. Cl.⁶ ................................................ A61K 38/20
[52] U.S. Cl. .............................. 424/85.2; 514/12; 514/21
[58] Field of Search .................................. 424/85.1, 85.2; 514/2, 12, 21, 886; 530/350, 351

[56] References Cited

U.S. PATENT DOCUMENTS 5,079,261   1/1992   Serhan et al. ........................ 514/552

FOREIGN PATENT DOCUMENTS

WO 94/04680   3/1994   WIPO.

OTHER PUBLICATIONS

Sigal et al. (1193), "Human 15–lipoxygenase: Induction by interleukin–4 and insights into positional specificity," *Chem. Abstr.* 119:680, Abstr. No. 119:137154y.

Nassar et al. (1994), "Induction of 15–Lipoxygenase by Interleukin–13 in Human Blood Monocytes," *J. Biol. Chem.* 269:27631–27634.

Hiltunen et al. (1995), "Induction of 15–Lipoxygenase mRNA and Protein in Early Atherosclerotic Lesions," *Circulation* 92:3297–3303.

Badr, K. (1992) *Kidney International* 42:(Suppl. 38); S–101–S–108.

Zurawski, G. et al. (1994) *Immunology Today* 15:19–26.

Conrad, D.J. et al. (1992) *Proc. Natl. Acad. Sci. U.S.A.* 89:217–221.

Katoh, T. et al. (1994) *Kidney International* 46:341–349.

McKenzie, A.N.J. et al. (1993) *Proc. Natl. Acad. Sci. U.S.A.* 90:3735–3739.

Sigal, E. et al. (1988) *Biochem. Biophys. Res.* 157:457–464.

*Primary Examiner*—Ponnathapura Achutamurthy
*Attorney, Agent, or Firm*—Greenlee, Winner and Sullivan, P.C.

[57] ABSTRACT

Methods are disclosed for inducing the production of 15-lipoxygenase (15-LO) in animal or human cells comprising monocytes via the administration of Interleukin 13 (IL-13). These methods are effective in therapy of inflammatory conditions responsive to products of 15-LO activity, including 15-s-hydroxyeicoiatetraenoic (15-S-HETE) and Lipoxin $A_4$ ($LXA_4$). Such administration directs intervention to specific and effectors of inflammation, rather than the current methods of symptomatic treatment.

19 Claims, 8 Drawing Sheets

USE OF IL-13 TO INDUCE 15-LIPOXYGENASE

The U.S. Government has certain rights in the invention based on research support provided by National Institutes of Health grant RO1 DK43883.

FIELD OF THE INVENTION

The invention relates to the regulation of products and end-effectors capable of anti-inflammatory effects, particularly with respect to monocyte/macrophage mediated inflammatory conditions of animals and humans.

BACKGROUND OF THE INVENTION

Inflammation is involved in a large number of physiological and pathological conditions affecting animals and humans. Inflammatory responses can usually be traced to an immune response to an antigen, allergen, irritant, endotoxin or to tissue damage. The process is complex, involving a large number of components, many of which display pleiotropic effects, many of which are amplifiers or inhibitors of other components. While many instances of an inflammatory response are well-controlled and self-limited, many pathologic conditions arise from uncontrolled or inappropriate responses, resulting in both acute and chronic conditions.

Inflammatory reactions differ not only as to the nature of the triggering event, but also in the types of cells mediating the response and in the biochemical nature of the end effectors. In particular, inflammation mediated by monocyte/macrophage activity can result in severe chronic or fatal conditions, including immune complex-initiated primary inflammatory disorders such as glomerulonephritis, chronic interstitial nephritis, interstitial pneumonitis, Crohn's disease, ulcerative colitis, osteoarthritis, biliary cirrhosis and the like, affecting other organ systems; also including connective tissue diseases such as rheumatoid arthritis, systemic lupus erythematosus and the like; further including secondary progressive inflammatory diseases in which the central cause of tissue destruction is uncontrolled inflammatory/fibrotic processes regardless of the nature of the initiating insult, for example chronic hepatitis, whether the initial insult be infectious, toxic, alcohol, etc., radiation induced chronic inflammations of lung, kidney, central nervous system, inflammations induced by crystal deposition, such as gout, and various forms of post-traumatic inflammatory injury, such as arthritis. Many prior therapeutic strategies have been directed at alleviating the various symptoms of the diseases, without affecting the process itself. In order to effectively intervene in the disease process itself, the present invention is based on a strategy of identifying specific pathogenic molecules and end-effectors so that agents able to inhibit or suppress these molecules can be developed.

The system of experimentally induced glomerulonephritis in the rat has yielded significant information as to the processes of disease development and the nature of the biochemical mediators of tissue destruction. See Badr, K. (1992) *Kidney International* 42(Suppl. 38): S-101-S-108, incorporated herein by reference. The presence of immune complexes in the glomerulus, regardless of their sources, routes of formation, or intraglomerular localization, inevitably and necessarily provokes a complement-mediated influx and activation of polymorphonuclear leukocytes (PMN). The very transient nature of the PMN infiltrate (first few hours following immune activation) renders it an infrequent finding in renal biopsies from patients with various forms of glomerulonephritis, leading to under-appreciation of the potential role of this early inflammatory event in the eventual outcome of disease. PMNs are, however, detected frequently when biopsies are performed during ongoing acute injury such as in patients with post-infectious glomerulonephritides. Characteristically, this initial wave of neutrophil infiltration/activation is replaced by monocyte infiltration and macrophage proliferation and activation. During this secondary ("autologous") phase, it is postulated that injury might be perpetuated not only by the consequences of activation/proliferation of macrophages and indigenous glomerular cells (particularly mesangial and epithelial cells), but also by fresh immune reactions to neo-antigens from host tissue exposed as a result of proteolytic and lipid peroxidative consequences of initial leukocyte activation and degranulation. The number of participating cells in the more chronic phase of immune injury, the interactions among these "stimulated" cell populations, and, consequently, the myriad of peptide and lipid-derived mediators which underlie cellular injury and the eventual replacement of normal glomerular architecture by extracellular matrix (fibrosis), is staggering. While strategies aimed at arresting glomerular injury by targeting the mediators of matrix expansion and scar formation show promise, the complexity of the "mediator soup" during this phase of injury and the various cell populations involved (including tubulointerstitial elements) present serious theoretical and practical obstacles to the development of effective therapeutic interventions.

Targeting the mechanisms which govern the severity of early immune-mediated injury rests on the premise that those diseases which most commonly lead to renal failure due to immune deposition are, for the most part, progressive over months to years, suggesting incremental phases of nephron loss. Evidence from pathologic examinations in several forms of glomerulonephritis indicates that injury is heterogeneous: the number of affected versus healthy glomeruli varies among patients, as well as over time in individual patients. Moreover, within individual glomeruli, lesions are often segmental with inflammatory reactions present in certain lobules, while others are totally normal. These data, as well as a clinical course characterized by steadily diminishing renal reserve over highly varying periods of time, suggest strongly that, in an individual patient, "early" injury is occurring continuously in some fixed proportion of nephrons. It is therefore reasonable to predict that institution of therapy which specifically targets those early events will arrest initial injury in those nephrons, albeit small in number, in which it is underway and, more importantly, prevent or abort its development in intact nephrons, despite the potential continued deposition or formation of immune complexes in these normal glomeruli. This latter assumption is based on the dramatic evidence from experimental studies indicating that mere deposition of antigen-antibody complexes in the glomerular capillary wall or mesangium, in the absence of cellular infiltration (as in leukocyte- or complement-depleted animals) or the capacity to generate arachidonate metabolites (as in fatty acid deficient animals), is without any detrimental acute or chronic consequences to glomerular structure and functions.

Leukocyte activation leads to the release of degradative enzymes, the generation of reactive oxygen species, and the biosynthesis of locally acting pro-inflammatory autacoids. Among the latter, oxygenated metabolites of arachidonic acid are recognized major products of leukocyte activation and exert potent biological effects on cellular functions. The arachidonate lipoxygenase (LO) family of enzymes catalyze the formation of highly potent biologic mediators in leukocytes and platelets. The predominant LO pathway in PMNs and macrophages is 5-LO, leading to the formation of leukotrienes (LTs) and 5-hydroxyeicosatetraenoic acid (5-HETE) (Samuelson, B. et al. (1987) *Science* 237:1171–1176). The sulfidopeptide LTs ($LTC_4$, $LTD_4$, and $LTE_4$) and the non-peptidyl $LTB_4$, elicit potent biological responses: $LTC_4$ and $LTD_4$ contract vascular, pulmonary, and gastrointestinal smooth muscle, and increase vascular permeability to macromolecules (Lewis, R. A. et al. (1984) *J. Clini. Invest.* 73:889–897; Samuelson, B. et al. (1987) supra. $LTB_4$ has minimal spasmogenic properties. Its primary target appears to be PMNs, which express specific high and low affinity receptors for $LTB_4$. Through the former, $LTB_4$ is the most potent chemotactic substance yet described for this cell and also increases PMN aggregation and adhesion to endothelium. Through the latter, it acts as a calcium ionophore, leading to PMN activation, stimulation of phosphoinositide turnover, release of lysosomal enzymes, and an increase in oxidative metabolism. In turn, activated PMNs are the best studied source of $LTB_4$ where its synthesis is coupled to activation of protein kinase C.

Direct effects of $LTC_4$, $LTD_4$ and $LTB_4$ on normal and inflamed glomerulus have been measured. $LTA_4$ is a product of 5-LO activity and serves as a precursor for both $LTC_4$ and $LTB_4$. The former requires the activity of a glutathione-S-transferase while the latter is the product of $LTA_4$ hydrolase. $LTD_4$ is the product of a γ-glutamyl transferase removing a glutamyl moiety from $LTC_4$. $LTD_4$ has a powerful effect of reducing glomerular capillary ultrafiltration coefficient acting on both normal and inflamed glomeruli. It is believed to be a major mediator of functional deterioration in glomerulonephritis. $LTC_4$ has been shown to reduce renal blood flow and glomerular filtration rate acting on normal kidney and is considered to act similarly in inflamed glomerulus. By contrast, $LTB_4$ has little direct effect on normal glomerulus. However it is a powerful chemotactic agent for PMNs. The role of $LTB_4$ in glomerulonephritis is seen as an indirect amplifier of leukocyte-dependent reductions in glomerular perfusion due to enhancement of PMN recruitment and activation.

An alternative metabolic pathway initiated by 15-lipoxygenase (15-LO) activity leads to compounds having antagonistic effects to the products of 5-LO activity. Hydroperoxidation of arachidonic acid by 15-LO leads to the formation of 15-S-hydroxyeicosatetraenoic acid (15-S-HETE). Dual lipoxygenation at both the 5 and 15 positions in activated neutrophils and macrophages yields a class of "lipoxygenase interaction products" [Lipoxins (LXs)] (Samuelson, B. et al. (1987), supra). Like 5-LO, 15-LO gene expression is restricted largely to leukocyte cell lines, but has also been detected in reticulocytes and airway epithelial cells. Using cDNA probes for human 15-LO, gene expression in glomerular cell lines has not been detected by northern analysis. Macrophages are a particularly rich source of 15-LO and hence of 15-S-HETE and LXs. Three biologically active lipoxins have been identified. $LXA_4$, (55,6R,155)-5,6,15-trihydroxy-7,9,13-trans-11-cis-eicosatetraenoic acid, $LXB_4$ (55,14R,155)-5,14,15-trihydroxy-6,10,12-trans-8-cis-eicosatetraenoic acid, and 7-cis-11-trans-$LXA_4$ (Samuelson, B. et al. (1987), supra; Nicolau, K. C. et al. (1989) *Biochem. Biophys. Acta* 1003:44–53; the pharmacological profile of their renal actions has been characterized recently (Katoh, T. et al. (1992) *Am. J. Physiol.* 263:F436–442). Lipoxin synthesis, like that of leukotrienes, can also occur via transformation of leukocyte-generated $LTA_4$ by either 15-LO or 12-LO in adjoining cells, such as mesangial cells or platelets.

Evidence for a generalized anti-inflammatory role for 15-LO products has been derived from clinical observations and experimental studies in vivo and in vitro. Administration of 15-S-HETE causes regression of psoriatic lesions in humans and significantly reduces the clinical severity of a canine arthritis model.

Figure 1:
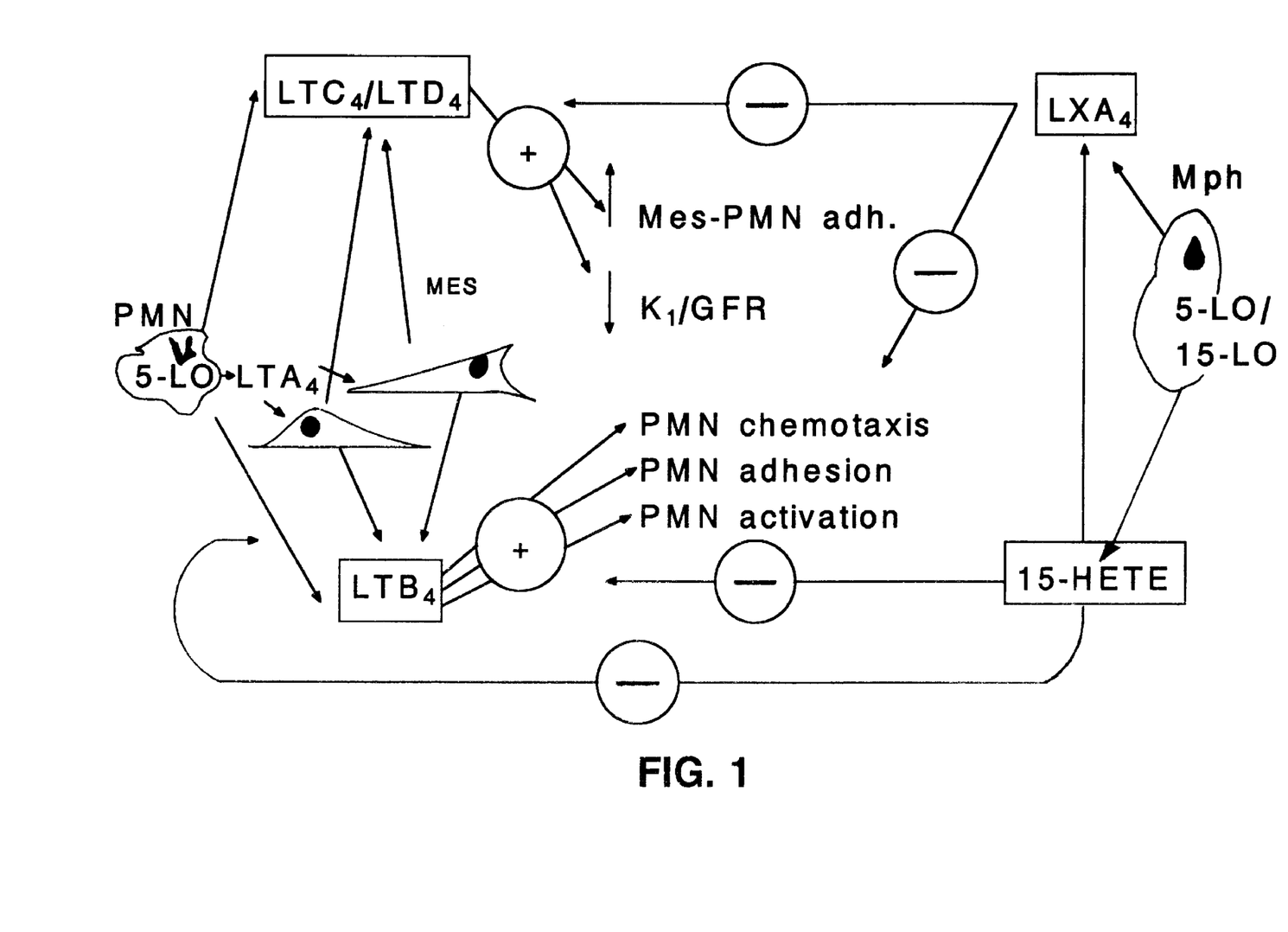
FIG. 1 is a diagram of the physiological effects and interactions between compounds whose biosynthesis involves 5-LO activity or 15-LO activity. Circles containing a + indicate an activation or stimulation, while circles containing a – indicate inhibition or repression. Compound abbreviations are defined in the text. Other abbreviations are: END=endothelial cell; MES=mesangial cell; adh=adhesion; Mph=macrophage; $k_f$/GFR=ultrafiltration constant/glomerular filtration rate.

The compound, 15-S-HETE, is a specific antagonist of $LTB_4$-induced chemotaxis of PMNs. Other chemotactically-active substances are not inhibited. 15-S-HETE also aborts leukocyte activation, abrogates adhesion of PMNs to endothelium and depresses $LTB_4$ synthesis by leukocytes. During experimental glomerulonephritis, production of $LTB_4$ reaches a peak about three hours after injury and declines to baseline levels after about 72 hours. In contrast, 15-S-HETE levels increase gradually over time up to two weeks, reaching levels consistent with the amounts required to achieve the antagonistic effects just described. The kinetics are consistent with the view that a slower-acting 15-LO pathway functions to inhibit and limit the intensity and scope of an inflammatory process, once the process has been initiated. The lipoxins, especially $LXA_4$, also have significant anti-inflammatory functions. For example, $LXA_4$ acts as an antagonist of the leukotrienes, having anti-chemotactic effect, and having direct vasorelaxation activity and augmentation of glomerular filtration rates. $LXA_4$ acts as a competitive inhibitor of $LTD_4$ receptor binding. $LXA_4$ also prevents or inhibits PMN adhesion to mesangial cells. A general schematic diagram of the counteractive effects of the 5-LO and 15-LO pathways in promoting or inhibiting inflammatory processes is shown in FIG. 1.

The manifold response modalities of the immune systems of mammals are regulated by a variety of secreted immunregulatory proteins termed cytokines. These include various colony stimulating factors, chemokines, interleukins and interferon-γ (IFN-γ). The characteristics of a variety of immune-type responses is largely controlled by the cell types involved and the cytokine network associated therewith in each case. For example, the involvement of the Th1 subset of helper T-cells leads to secretion of IFN-γ and interleukin-2 (IL-2) which appear to promote a delayed-type hypersensitivity response. Another type of response, mediated by Th2 subset of helper T cells, is characterized by secretion of IL-4 and IL-5, which act to promote antibody responses. For a recent review, see Mosmann, T. R. et al. (1989) *Annu. Rev. Immunol.* 7: 145–173. There is a complex series of positive or negative responses to each set of cytokines by many cell types in the immune system. Much has been learned concerning the function of cytokine networks. However new findings and newly discovered cytokines often require those skilled in the art to revise their theories of cytokine network interactions.

Interleukin 13 (IL-13) was originally discovered from a library of induction-specific cDNAs produced by a helper T-cell line. Its nucleotide sequence and deduced amino acid sequence were known before much was known about its function. Subsequent functional studies have shown that IL-13 shares many functional attributes with IL-4, but with certain significant differences. For a recent review, see Zurawski, G. et al. (1994) *Immunology Today* 15:19–26. Both IL-4 and IL-13 promote immunoglobulin switching to increase IgE production, suggesting a possible role in stimulating allergic reactions. On the other hand, both IL-4 and IL-13 down-regulate the production of proinflammatory cytokines by monocytes, including IL-1α, IL-1β, IL-6, IL-8, macrophage inflammatory protein 1α (MIP-1α), tumor necrosis factor-α (TNF-α), granulocyte-macrophage colony stimulating factor (GM-CSF) and granulocyte colony stimulating factor (G-CSF). Also similarly to IL-4, IL-13 up-regulates IL-1 receptor antagonist (IL-1ra), a protein having anti-inflammatory activity. There is evidence that the receptors of IL-4 and IL-13 are similar or perhaps share a common subunit. For example, the modified human IL-4, Y124D, acts as a receptor antagonist for both IL-4 and Il-13. However the IL-4 binding protein, which may be IL-4 receptor, does not bind IL-13.

There are significant differences between IL-13 and IL-4 activity. Most notably, IL-13 has no ability to activate T-cells, while IL-4 activates both T-cells and monocytes. Il-13 reportedly inhibits HIV replication in monocytes while IL-4 may not, since reports conflict. Murine IL-13 induces proliferation of mouse plasmacytoma B9 cells, although these cells respond minimally to mouse IL-4.

Early evidence that IL-13 stimulated an IgE response encouraged the concept that IL-13 inhibitors might be useful for treatment of allergic conditions. See, e.g. International Publication Number WO 94/04680 which discloses a cDNA sequence encoding human IL-13 and suggests inhibition of IL-13 activity for treating allergic reactions.

Both IL-4 and IL-13 have been postulated to have anti-inflammatory properties, based primarily on their capacity to suppress production of proinflammatory cytokines and to upregulate IL-1ra production by monocytes/macrophages (Zurawski et al. (1994), supra). Nevertheless, a biochemical understanding of IL-13 activity has heretofore prevented rational therapeutic design for use of IL-13 in specific conditions. Although IL-4 has been reported to induce 15-LO synthesis (Conrad, D. J. et al. (1992) *Proc. Nat'l Acad. Sci. U.S.A.*, 89:217–221; Katoh, T. et al. (1994) *Kidney International* 46:341–349), no evidence for such activity by IL-13 has been reported prior to the present invention.

SUMMARY OF THE INVENTION

The present invention is based on the discovery that IL-13 induces 15-LO in human monocytes. Surprisingly, it has been found that IL-13 is about ten-fold more active, on a molar basis, than IL-4 in inducing 15-LO. Il-13 is therefore an effective therapeutic for inflammatory conditions responsive to products of 15-LO activity, including 15-S-HETE and $LXA_4$. By enhancing endogenous pathways leading to synthesis of endogenous anti-inflammatory molecules, administration of IL-13 results in inhibition of the end effectors of the inflammatory process itself. The underlying strategy is therefore to direct intervention to specific pathogenic molecules, rather than the current method of treating symptoms of inflammation.

It will be understood by those skilled in the art that a variety of enzymes, cofactors and intermediates operate in the synthesis of the anti-inflammatory end effectors which result from induction of 15-LO activity. It is a well-known principle of control of biochemical pathways that primary control is vested in the first enzymatic step of the series of steps leading to the end product. In the case at hand, synthesis of anti-inflammatory effectors including but not limited to 15-S-HETE and the lipoxins is initiated by 15-lipoxidation of arachidonic acid. Subsequent reactions involve the activity of hydrolases, transferases, dehydrogenases, hydroperoxidases and the like, leading to the above-cited anti-inflammatory end effectors. It is possible that other products of 15-LO-initiated reaction sequences having anti-inflammatory properties remain to be discovered. It is by now well-established that a dichotomy exists between the set of compounds synthesized from products of 5-LO and those from products of 15-LO. The former are potent pro-inflammatory substances, while the latter have potent anti-inflammatory effects. The 15-LO pathway therefore serves as a regulator of inflammation, limiting the severity and duration of an inflammatory response (Badr, K. F. (1992), supra). Pathologic conditions occur when the inflammation is uncontrolled, leading to tissue destruction. It is now possible to effectively induce the 15-LO pathway by administration of an effective amount of IL-13, re-establishing control of an inflammatory response which has, for whatever reason, become unbalanced. Other modes of intervention, e.g., direct administration of $LXA_4$ and its derivatives, have also been disclosed (Serhan et al., U.S. Pat. No. 5,079,261).

In addition to induction of 15-LO, IL-13 has been found to be a potent down-regulator of enzymes of the 5-LO pathway. In particular, IL-13 is a potent inhibitor of the expression of $LTA_4$ hydroxylase, the enzyme which converts $LTA_4$ to $LTB_4$. Maximal potency of IL-13 is demonstrably greater than that of IL-4. Similar results have been obtained for induction of 5-LO itself. The down-regulating effects of IL-13 are independent of the known down-regulatory effects of IL-13 on pro-inflammatory cytokines, since the levels of enzyme expression are below the control levels of unstimulated monocytes.

DETAILED DESCRIPTION OF THE INVENTION

The present invention provides a way of treating or alleviating certain inflammatory conditions, those which are responsive to the direct or consequential products of 15-LO activity. The direct or consequential products of 15-LO activity include, without limitation, 15-S-HETE, $LXA_4$, other lipoxins and other compounds whose synthesis includes a step catalyzed by 15-LO. The method of treatment includes administration of IL-13, a potent inducer of 15-LO activity, or a variant or analog of IL-13 having comparable 15-LO inducing activity. Representative inflammatory conditions responsive to such treatment include glomerulonephritis, chronic interstitial nephritis, interstitial pneumonitis, Crohn's disease, ulcerative colitis, osteoarthritis, biliary cirrhosis and the like, affecting other organ systems; also including connective tissue diseases such as rheumatoid arthritis, systemic lupus erythematosus and the like; further including secondary progressive inflammatory diseases in which the central cause of tissue destruction is uncontrolled inflammatory/fibrotic processes regardless of the nature of the initiating insult, for example chronic hepatitis, whether the initial insult be infectious, toxic, alcohol, etc., radiation induced chronic inflammations of lung, kidney, central nervous system, inflammations induced by crystal deposition, such as gout, and various forms of post-traumatic inflammatory injury, such as arthritis. Treatable conditions include those mediated by monocyte/macrophage activity, as contrasted with, e.g., allergic reactions.

Administration of IL-13 can be accomplished by any means likely to bring the cytokine into contact with the target cells, which are primarily monocytes. Systemic administration is feasible, for example by intravenous administration, especially if the inflammation is generalized. Localized administration is preferred whenever inflammation is confined to a target organ such as the kidney in the case of glomerulonephritis. In such cases, administration by intra-arterial route, e.g., into the renal artery, can be preferable. Such administration has the advantage of being fast and having greatest effect on the target tissue, which may be very important in glomerulonephritis where the rate of tissue destruction can be rapid. Localized delivery of IL-13 also has the advantage that the opportunity for side effects, such as enhanced allergic responses, is reduced. Long term administration can be accomplished by means of implanted slow release compositions comprising IL-13. Ex vivo administration of IL-13 to whole blood or isolated leukocytes is also contemplated where indicated, for example where it is desired to minimize the amount of free IL-13 in the subject's circulation.

IL-13 can be administered as a solution dissolved in any pharmaceutically acceptable diluent, including normal saline, buffered saline and the like. Effective dosage ranges from daily administration of about 10 ng/kg of body weight to about 1 mg/kg. The daily dose is preferably administered at intervals rather than as a single dose. For some indications metered infusion will be preferred. As previously noted, sustained release formulations and implants can be employed to provide a steady elevated level of IL-13 for a desired time period. For ex vivo administration, dosages can range from 10 pM to 1 $\mu$M.

The effectiveness of therapy can be evaluated by the standard clinical measurements which are applied to the disease under treatment. For example, glomerulonephritis treatment can be monitored by measurement of glomerular filtration rate (GFR), by urinary protein excretion, by urinary sediment and the like, as well as by more sophisticated tests such as dextran seiving tests and measurement of ultrafiltration coefficient. In treatment of inflammations involving other organ systems, appropriate clinical tests to measure normal and abnormal function associated with inflammation are well known to those skilled in the art.

Human IL-13 is preferred for human therapy, to minimize the likelihood of developing antibodies to the protein. Although IL-13 can in principle be purified from a human source such as whole blood, the preferred source is synthesis by recombinant means, e.g. as described by McKenzie, A. N. J. et al. (1993) *Proc. Natl. Acad. Sci. USA* 90:3735 14 3739. Although sites for glycosylation exist, the unglycosylated protein is active. Various preparations of IL-13 may contain varying proportions of active and inactive forms. Activity of different preparations can be normalized by activity in a cell proliferation assay using human TF1 cells. The dose corresponding to 50% of maximal efficacy ($ED_{50}$) can be determined. It will be understood that various modifications to the IL-13 amino acid sequence can be made. The resulting modified IL-13 analogs can also be used as anti-inflammatory agents provided they have comparable (or greater) 15-LO inducing activity. It is also recognized that small molecular analog compounds able to bind the IL-13 receptor can also be developed. Such compounds may retain 15-LO inducing activity, and if so, can serve as anti-inflammatory agents. The invention therefore subsumes all such modified IL-13 analogs and compounds having IL-13 receptor binding activity, provided such analogs and compounds have useful 15-LO inducing activity.

Figure 2:
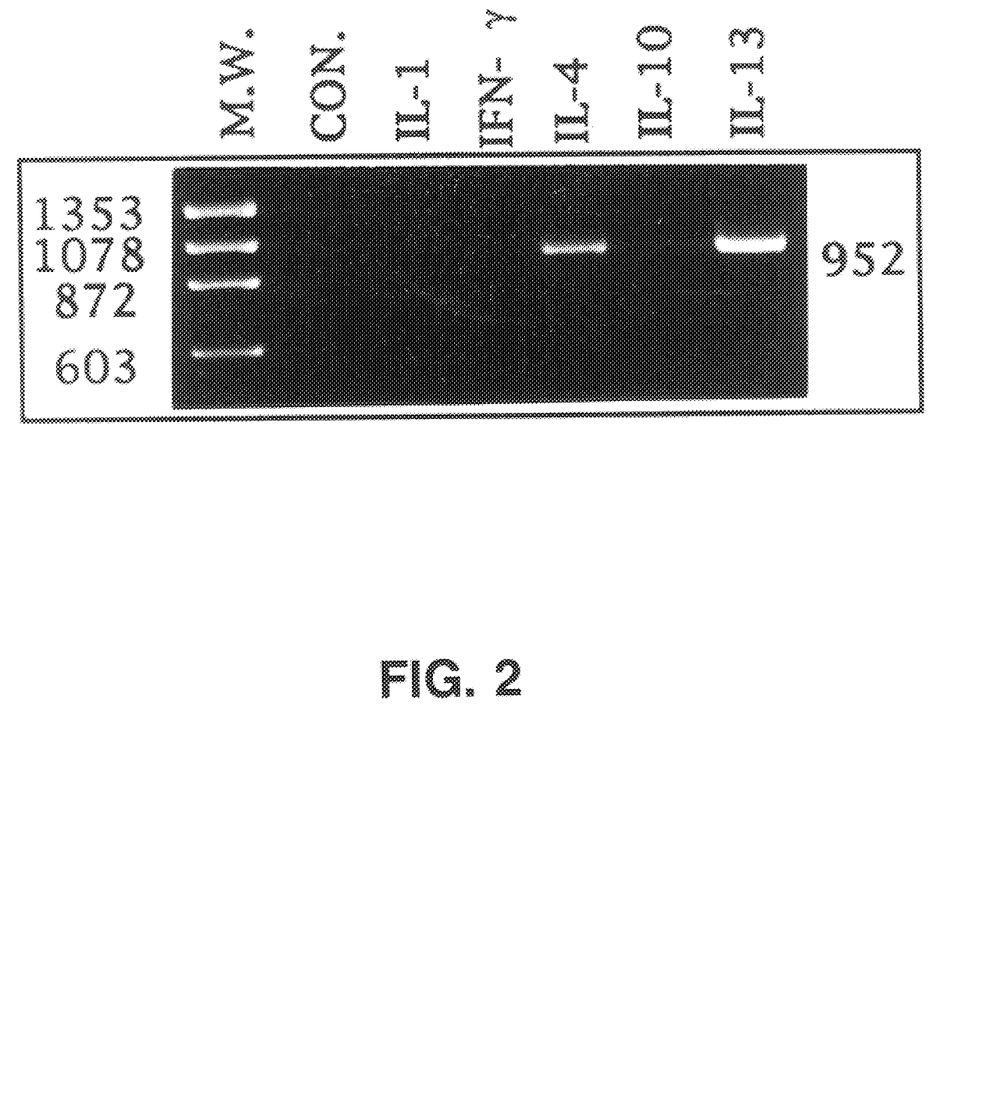
FIG. 2 shows results of agarose gel electrophoresis of DNA detected by ethidium bromide staining. Human monocytes were treated with various cytokines to determine the effect of the treatment on expression of 15-LO in RNA as detected by the RT-PCR method. M.W. refers to standard molecular weight markers whose molecular weight is given in the left margin. CON refers to a control reaction in which cells were not exposed to added cytokines. Other cytokine treatments as indicated for each column. Molecular weight of 15-LO in RNA amplified by RT-PCR is shown in right margin.

The experimental findings which underlie the present invention are set forth in detail below. The experimental procedures are described in the Examples section. Isolated monocytes from healthy human volunteers were exposed to various cytokines and then assayed for the presence of 15-LO MRNA expression, 15-LO protein expression and 15-S-HETE synthesis. In FIG. 2, expression of 15-LO mRNA was measured by a reverse transcriptase polymerase chain reaction (RT-PCR) to amplify 15-LO coding sequences using primers specific for 15-LO cDNA. 15-LO mRNA was detected in total RNA from monocytes incubated with IL-13 (100 pM) or with IL-4 (100 pM) for 36 h. Serum-enriched medium control (CON), IL-1β (50 pM), IFN-γ (100 pM) and IL-10 (1 nM) all failed to induce 15-LO mRNA.

Figure 3A:
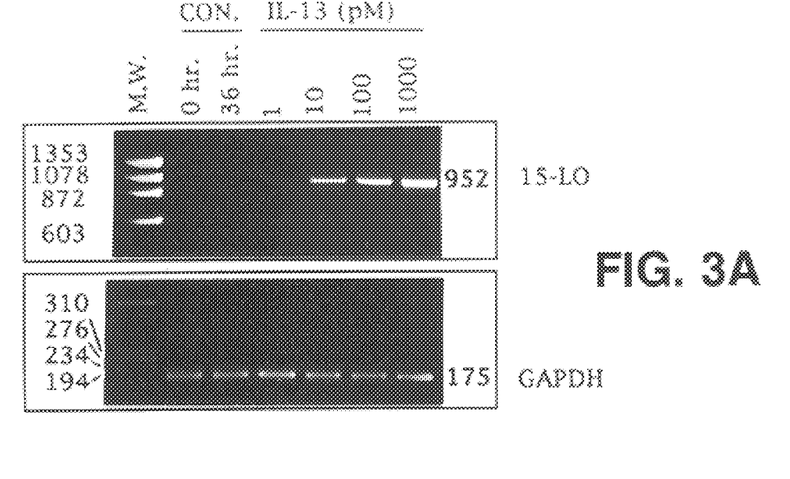
FIG. 3A shows the results of agarose gel electrophoresis of DNA detected by ethidium bromide staining. Human monocytes were treated with a range of indicated concentrations of IL-13, as shown in the upper panel. The lower panel shows results of a control reaction measuring GAPDH mRNA expression.
Figure 3B:
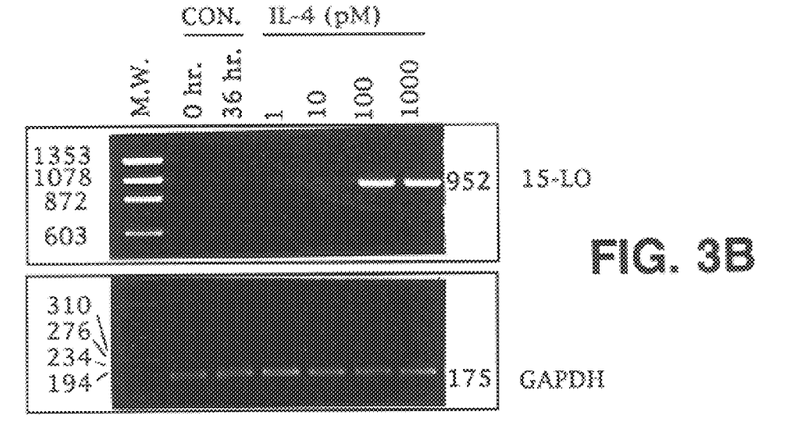
FIG. 3B shows results as in FIG. 3A except cells were treated with IL-4 at the indicated concentrations.
Figure 3C:
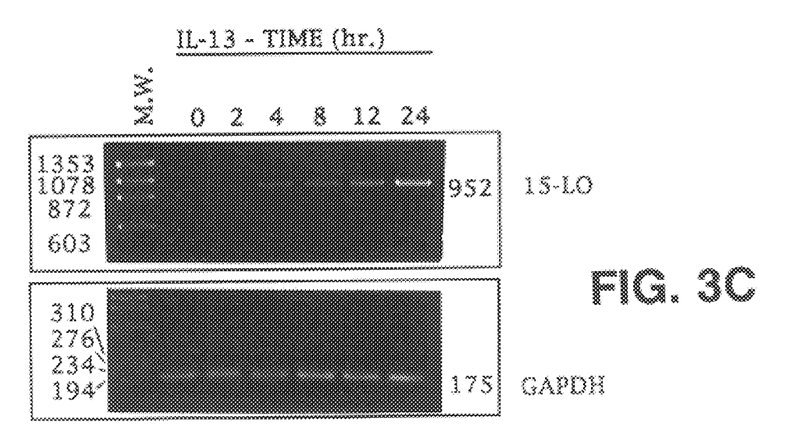
FIG. 3C shows results as in FIG. 3A except samples were measured at different time intervals after Il-13 treatment, as indicated.

FIG. 3A shows the dose response of monocytes to IL-13 treatment after 36 h induction. Detectable 15-LO mRNA was induced in response to as little as 1 pM IL-13. The control panel shows that glyceraldehyde-3-phosphate dehydrogenase (GAPDH) mRNA was detectable at comparable levels in every case. FIG. 3B shows the dose response to IL-4. By contrast, detectable 15-LO MRNA was detectable at 10 pM IL-4 or higher. IL-13 was therefore about 10 times more potent as an inducer of 15-LO mRNA than IL-4, on a molar basis. The time course of induction by 100 pM IL-13 is shown in FIG. 3C. 15-LO mRNA expression was detectable as early as 4 h after induction. A series of conventional Northern blot experiments confirmed qualitatively the results just described. Further, the Northern blot study demonstrated that IFN-γ blocks induction of 15-LO mRNA by IL-13.

Figure 4:
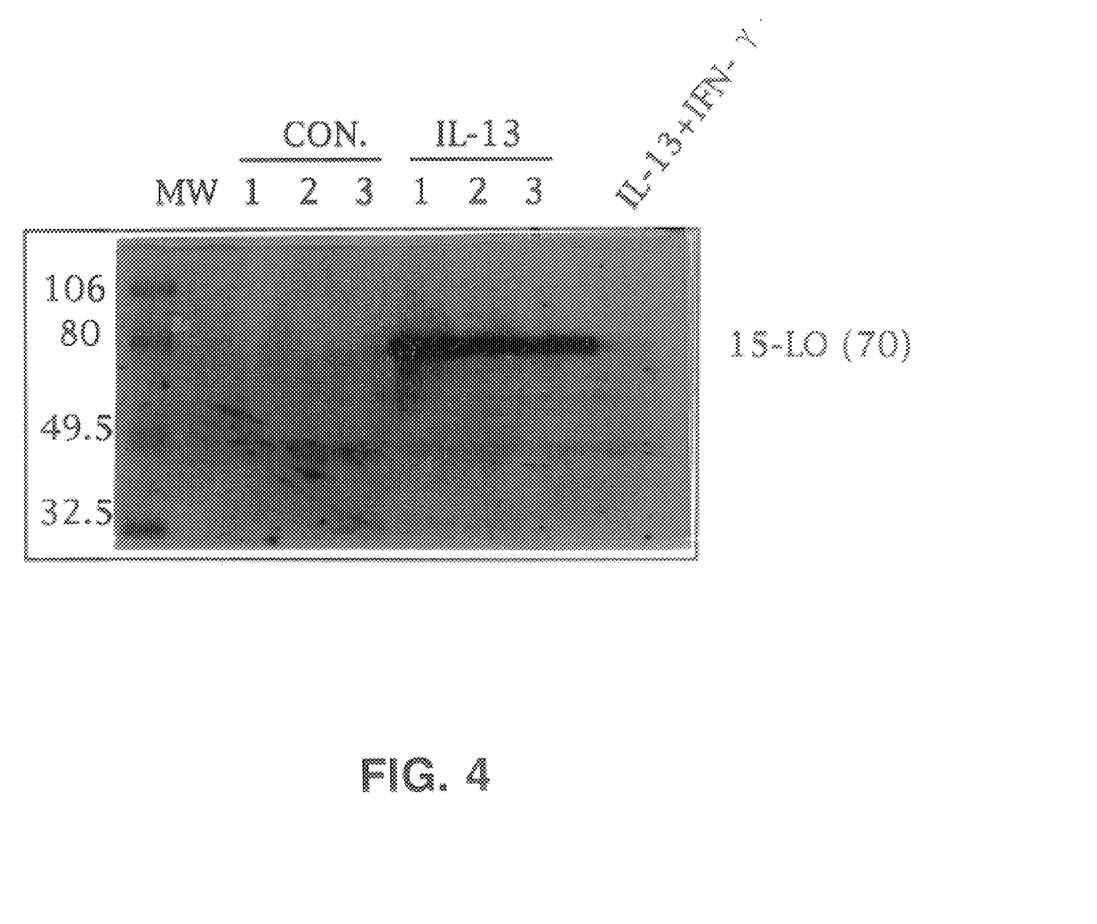
FIG. 4 is a Western blot to detect the presence of 15-LO in cells treated with IL-13, untreated ("CON.") or treated with a combination of IL-13 and IFN-γ. Molecular weight markers ("MW") are shown together with their known molecular weights on the left- most lane. 15-LO(70) in the right margin indicates the expected position of the 15-LO band on the gel.

In order to determine whether the effect of IL-13 on 15-LO MRNA expression translates to an effect on 15-LO protein synthesis, total cellular protein from control and IL-13-treated monocytes, as well as monocytes treated with both IL-13 and IFN-γ, was subjected to Western blot analysis using anti-human 15-LO antibody. These immunoblots detected 15-LO as a single immunoreactive band at ≈70 KDa in IL-13 treated monocytes (FIG. 4). In marked contrast, no 15-LO hybridization signal was detected in lysate from control monocytes or monocytes incubated with both IL-13 and IFN-γ.

Incubation of monocytes with IL-13 in the presence of arachidonic acid (100 μM) led to enhanced production of 15-S-HETE. In supernatants of IL-13-stimulated monocytes, a peak co-eluting with 15-S-HETE standard was detected but was absent in supernatants of control cells. The identity of 15-S-HETE was confirmed by negative ion-chemical ionization mass spectrometry analysis. Quantitation of the generated 15-S-HETE by this method, expressed as ng of 15-S-HETE/mg of cellular protein/min, revealed an average 43-fold increase in IL-13-treated samples versus controls (206.3 ng/mg/min and 4.8 ng/mg/min respectively).

Figure 5:
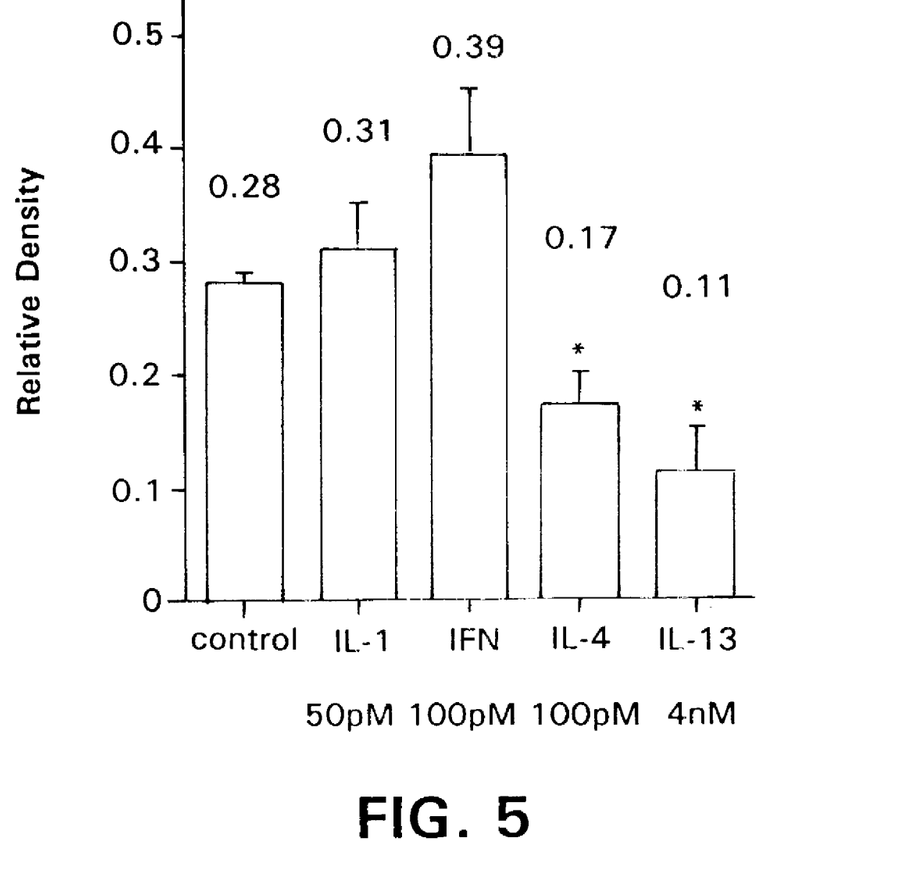
FIG. 5 shows measurements of relative band density of $LTA_4$ hydroxylase mRNA expression after RT-PCR, gel electrophoresis and ethidium bromide staining. Ordinate and numbers atop each bar are relative staining density values. Each bar represents treatment of monocytes by the indicated cytokine present at ten times its respective $ED_{50}$ value.
Figure 6:
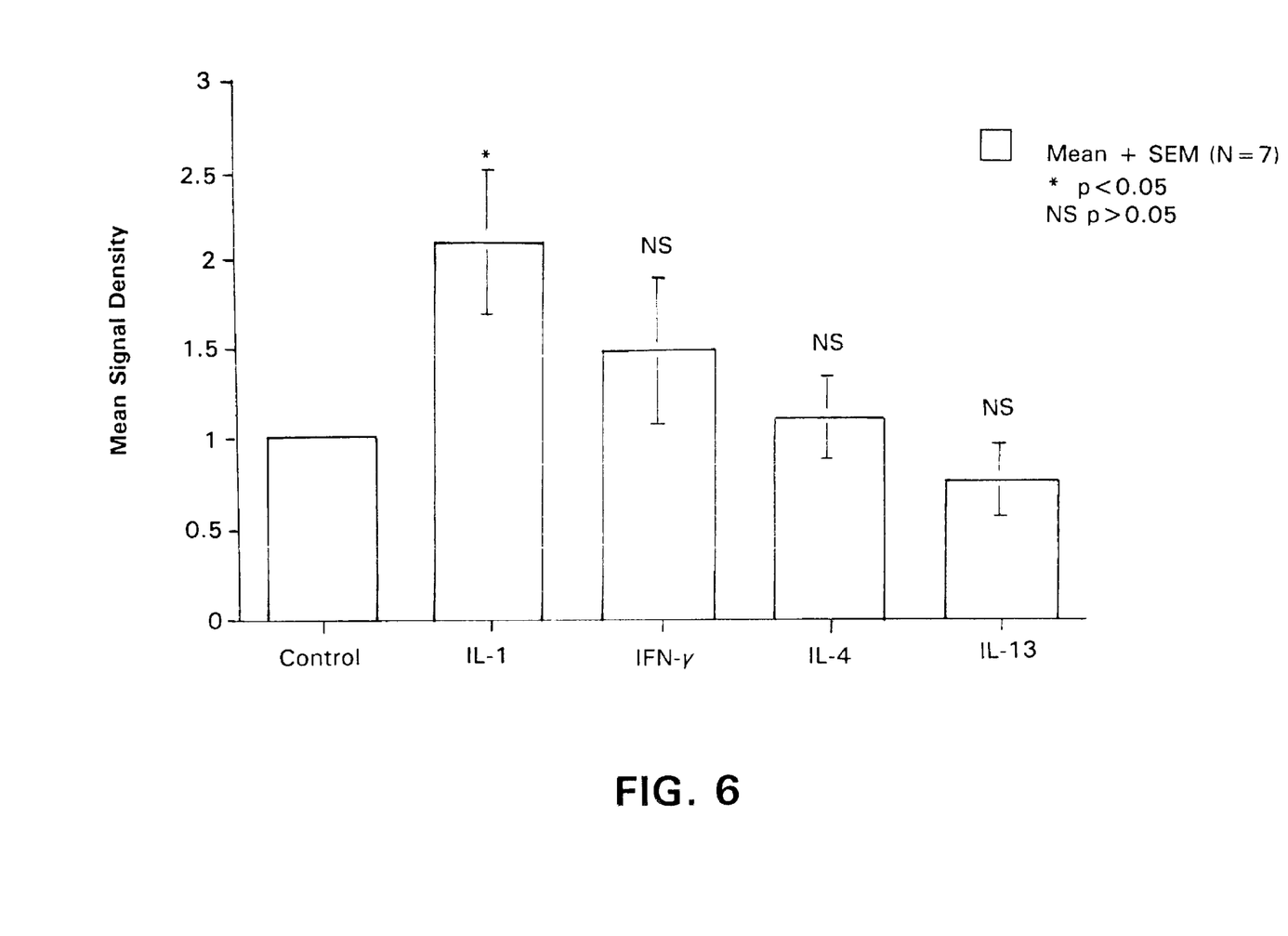
FIG. 6 is a bar graph of signal densities of 5-LO mRNA expression after RT-PCR, gel electrophoresis and ethidium bromide staining. The bar heights represent signal densities in arbitrary units proportional to the quantity of DNA in the band corresponding to 5-LO DNA. Each bar represents treatment of monocytes by the indicated cytokine present at ten times its respective $ED_{50}$ value.
Figure 7:
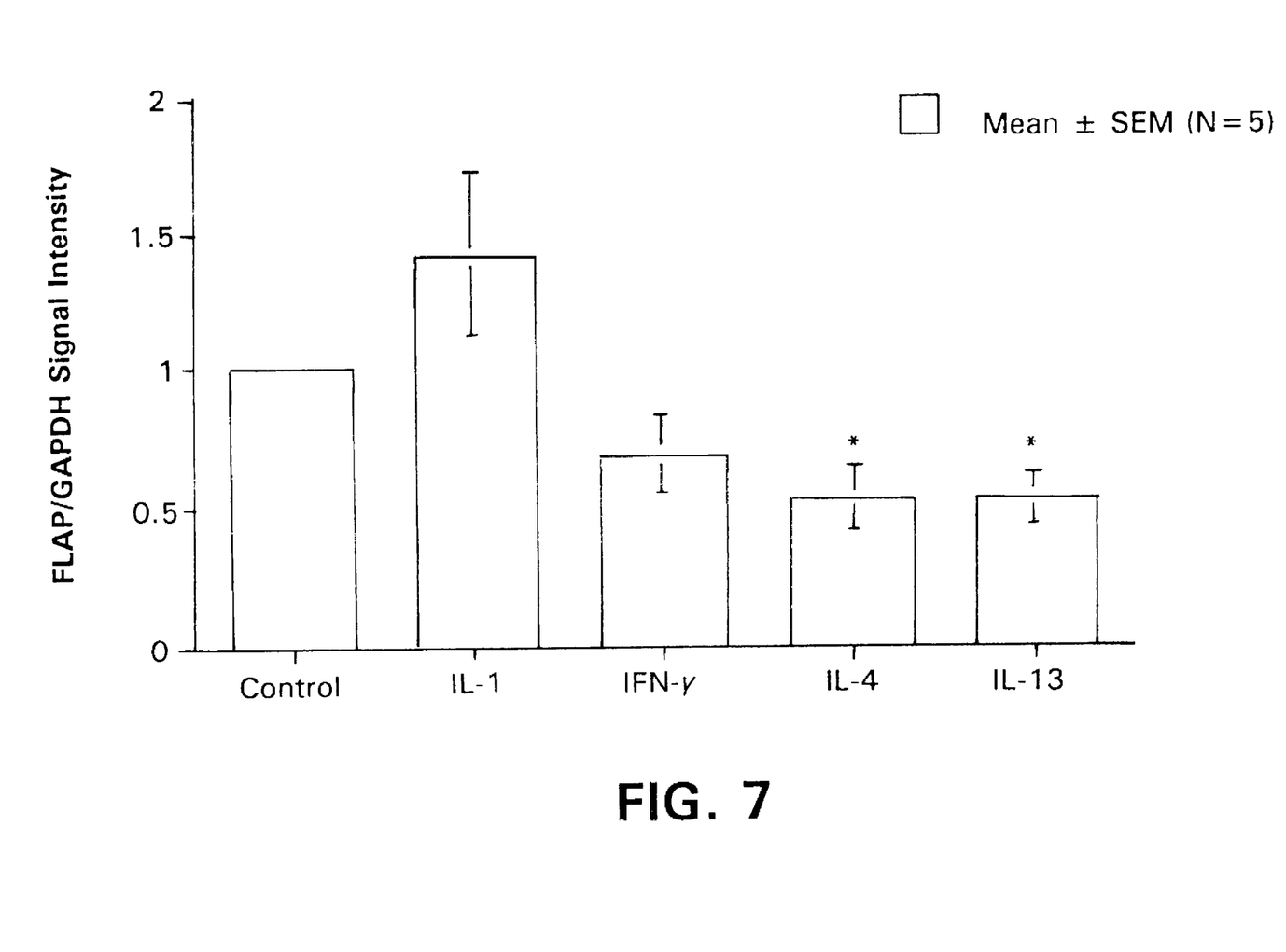
FIG. 7 is a bar graph of signal densities of FLAP mRNA expression relative to GAPDH mRNA expression after RT-PCR, gel electrophoresis and ethidium bromide staining. The bar heights represent signal density in arbitrary units proportion to the quantity of DNA in the bands corresponding to FLAP DNA and GAPDH DNA. Each bar represents treatment of monocytes by the indicated cytokine present at ten times its respective $ED_{50}$ value.
Figure 8:
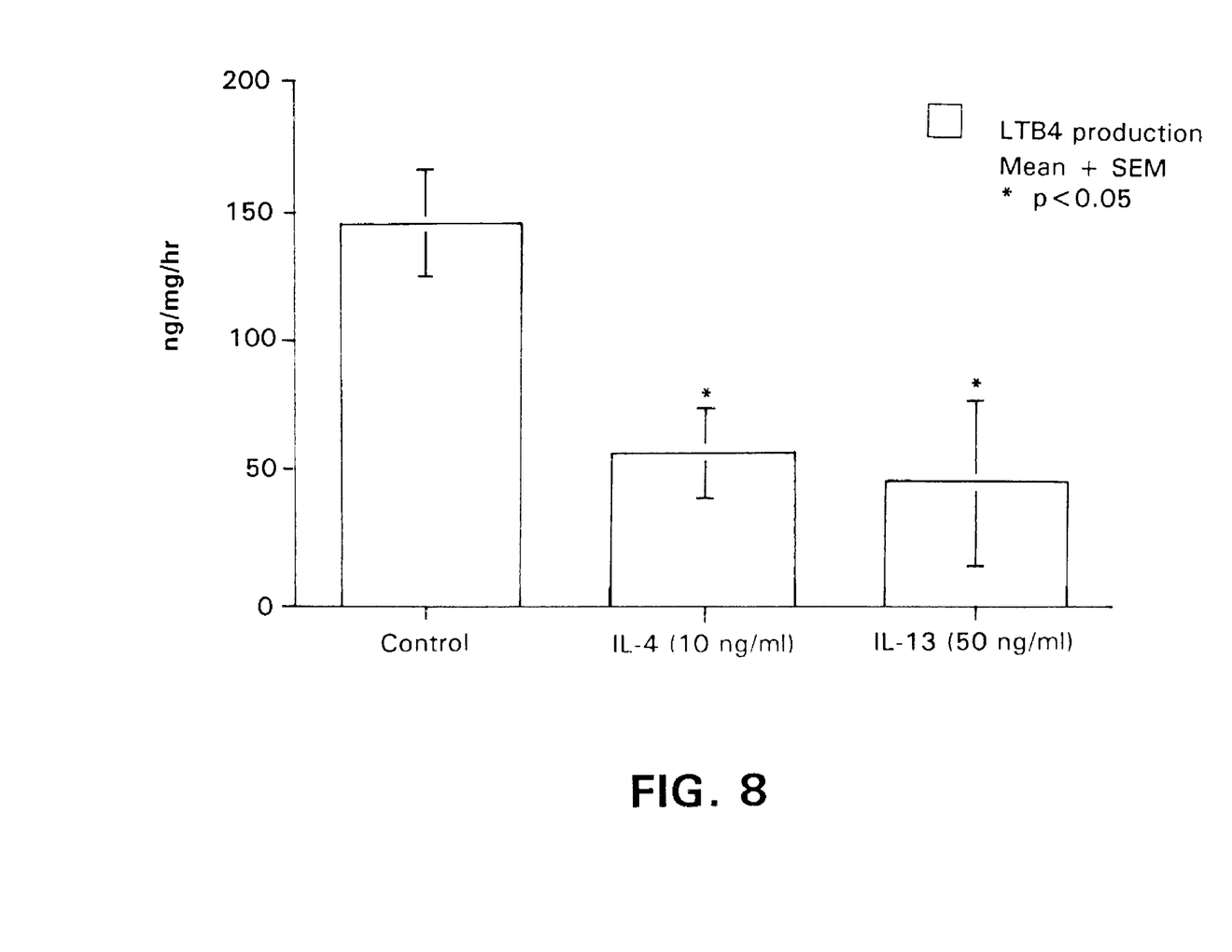
FIG. 8 is a bar graph of the rate of $LTB_4$ production by monocytes incubated with either IL-4 or IL-13 at indicated concentrations relative to untreated control cells. Bar heights represent ng $LTB_4$/mg/hr produced after 36 h incubation of cells with cytokine.

Studies on the effects of various cytokines on enzymes of synthesis of pro-inflammatory compounds reveal that IL-13 is an inhibitor of their expression. FIG. 5 shows results of RT-PCR measurement of $LTA_4$ hydroxylase mRNA expression in monocytes after 36 h incubation with various cytokines at 10 times their respective $ED_{50}$ concentrations. The data represent maximal effects rather than threshold effects. Both IL-1 and IFN-γ stimulate $LTA_4$ hydroxylase expression, while IL-4 and, more pronouncedly, IL-13 repress expression compared to untreated control cells. FIG. 6 shows the results of cytokine effects on 5-LO expression. Both IL-1 and IFN-γ stimulate expression. IL-4 had no apparent effect, while IL-13 repressed 5-LO mRNA expression. FIG. 7 shows results of cytokine treatment on 5-lipoxygenase activating protein (FLAP) mRNA expression, expressed relative to GAPDH mRNA as a constitutive control. Both IL-4 and IL-13 had a repressive effect on expression, with comparable maximal effects. As a test to determine whether repressing de novo expression of the enzymes of biosynthesis also reduces the level of inflammatory end effectors, the levels of $LTB_4$ were measured after treatment of monocytes with IL-4 or IL-13 for 36 h. FIG. 8 shows the result of one such test, showing comparable maximal effect for both cytokines.

Details of the experimental procedures are set forth in the following Examples. The cytokines purchased were recombinant human IL-1, IL-4, IL-10 (R&D Systems, Minneapolis, Minn.), and IFN-γ (Boehringer Mannheim, Mannheim, Germany). Human IL-13 was a gift from Dr. R. de Waal (DNAX, Palo Alto, Calif.). The $ED_{50}$ values of the cytokines determined by cell proliferation assays were as follows: IL-β, 3–10 pg/ml (murine helper T-cell line D10.G4.1); IL-4, 1–2 ng/ml (murine Th-2 cell line); and IL-10, 0.5–1.0 ng/ml (murine mast cell line). IL-13 had a specific activity of $1.6 \times 10^6$ units/mg (assayed on human TF1 cells), and IFN-γ had a specific activity of $2 \times 10^7$ units/mg (inhibition of cytopathic effect of EMC virus on human amniotic cells). Rabbit anti-human recombinant reticulocyte 15-LO polyclonal antibody was a gift from Dr. Elliot Sigal (Syntex, Palo Alto, Calif.). GeneAmp RNA PCR kits were purchased from Perkin-Elmer Corp., Norwalk, Conn.; DNA oligolabeling kits were obtained from Pharmacia Biotech Inc., Piscataway, N.J., and ECL kits for Western blot analysis were obtained from Amersham Corp., Arlington Heights, Ill.

EXAMPLE 1

Monocyte Isolation and Incubation

Fresh peripheral blood mononuclear cell packs were obtained from healthy volunteers (American Red Cross, Atlanta, Ga.) and subjected to Ficoll-Hypaque (Life Technologies, Inc., Gaithersburg, Md.) density gradient centrifugation. The mononuclear cell layer was recovered, washed with Hanks' balanced salt solution and suspended at $15 \times 10^6$ cells/ml in RPMI 1640 medium supplemented with L-glutamine (200 mg/liter), and antibodies (penicillin, streptomycin). Cells were then adhered to 100-mm polystyrene tissue culture plates for 3 h at 37° C. in the presence of 5% $CO_2$. The nonadherent cells were removed by washing the plates 3 times with phosphate-buffered saline, and the adherent cells were incubated in 10% fetal calf serum-enriched RPMI medium for 36 h (37° C., 5% $CO_2$) in the presence or absence of cytokines. Cytokine concentrations in culture were initially chosen to be approximately 10 times the manufacturer's reported $ED_{50}$. More than 90% of the adherent cells stained positive for monocyte nonspecific esterase, and more than 92% were viable by trypan blue dye exclusion. Cell viability following 36 h of incubation with and without cytokine was around 90–92%.

EXAMPLE 2

RNA Isolation and Analysis

Total cellular RNA was purified from adherent peripheral blood monocytes by the Chomczynski method(*Anal. Biochem.* 162:156–159) using the RNAzol reagent (Biotecx Laboratories, Houston, Tex.). 15-LO mRNA was amplified by reverse transcriptase polymerase chain reaction (RT-PCR) using GeneAmp RNA kits (Perkin-Elmer Corp.) and human 15-LO specific oligonucleotide primers. The respective nucleotide sequences of the sense and antisense primers were 5'-GAGTTGACTTTGAGGTTTCGC-3' (SEQ ID NO:1) and 5'-GCCCGTCTGTCTTATAGTGG-3' (SEQ ID NO:2). Primer pairs were designed using PCRPLAN software (PC/GENE, Intelligenetics, Inc., Mountain View, Calif.) based on the published cDNA sequence of the 15-LO gene (Sigal, E. et al. (1988) *Biochem. Biophys. Res.* 157:457–464). The PCR reaction was carried out using the following parameters: number of cycles, 35; annealing temperature, 58° C. for 1.5 min; extension temperature, 72° C. for 1.5 min; magnesium concentration, 1 mM. PCR products were then analyzed by 2% agarose gel electrophoresis and ethidium bromide staining. The DNA band corresponding to the 15-LO DNA segment was identified by its predicted size (952 bp). In view of the high degree of homology among cDNA sequences of 5-LO, 12-LO and 15-LO (Katoh, T. (1994), supra), the primer pairs were selected from regions of 15-LO DNA that share the least degree of homology with the other lipoxygenases. These primers proved to be specific for 15-LO as they amplified the expected DNA segment from 15-LO cDNA but did not amplify any segments from 5-LO or 12-LO cDNA.

EXAMPLE 3

Northern Blot Hybridization

Expression of 15-LO mRNA was also analyzed by Northern hybridization. Total cellular RNA (20 μg) was electrophoresed on a 1% formaldehyde-agarose gel, transferred to Hybond-N+ membrane (Amersham Corp., Arlington Heights, Ill.), and covalently linked by ultraviolet irradiation using a UV cross-linker (Stratagene, La. Jolla, Calif.). Radiolabeled probe was prepared using 100 ng of full-length 15-LO cDNA in a standard protocol for oligolabeling with [$^{32}$P]dCTP (oligolabeling kit, Pharmacia). Approximately $1-2 \times 10^6$ cpm of labeled probe (specific activity $\approx 1 \times 10^9$ dpm/μg DNA) were used per ml of hybridization solution. Hybridizations were performed at 42° C. for 16 h following which the membrane was washed with a final stringency of 0.2×SSC, 0.1% SDS at 55° C. Autoradiography was performed using Hyperfilm-MP (Amersham, Corp.) with an intensifying screen at −70° C. for 8 h. These RNA blots were afterwards stripped using boiling water with 1% SDS and then reprobed for GAPDH mRNA to ensure equal loading of RNA.

EXAMPLE 4

Western Blot Analysis

Following 36 h of incubation, adherent monocytes were washed in phosphate-buffered saline, suspended in lysis buffer (50 mM HEPES, 1% Triton X-100, 50 mM NaCl, 50 mM NaF, 10 mM sodium pyrophosphate, 5 mM EDTA, 1 mM $Na_3VO_4$, 1 mM phenylmethylsulfonyl fluoride, 10 mg/liter aprotinin, 10 mg/liter leupeptin), and sonicated for 10 s. Cell debris was separated from solubilized protein by centrifugation at 1200×g for 10 min. Protein in the supernatant was quantitated using the Bio-Rad protein assay technique (Bio-Rad, Hercules, Calif.). 30 μg of total protein was then separated by 7.5% SDS-polyacrylamide gel electrophoresis and transferred to nitrocellulose membrane using Trans-Blot SD electrophoretic transfer cell (Bio-Rad). The membrane was probed with a rabbit IgG anti-human recombinant reticulocyte 15-LO antibody for 1 h. The hybridization signal was detected using Enhanced Chemiluminescence (ECL) detection reagents (ECL, Amersham, United Kingdom). The ECL reagents were added as described by the manufacturer, and autoradiography was performed at room temperature for 1 min.

EXAMPLE 5

Measurement of 15-S-HETE

In these experiments, monocytes were incubated with medium alone or with IL-13 for 36 h. Cells were then washed 2 times with phosphate-buffered saline and incubated for 30 min in complete RPMI 1640 medium in the presence of 100 μM arachidonic acid (Nu-Check-Prep, Inc., Elysian, Minn.). Adherent cells were quantitated for cellular protein by the Bio-Rad protein assay technique. Quantitation of 15-S-HETE in the supernatants was carried out by reverse-phase high performance liquid chromatography (30) followed by negative ion-chemical ionization mass spectrometry analysis. The results were expressed as ng of 15-S-HETE generated per mg of cellular protein/min.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i ) MOLECULE TYPE: other nucleic acid
        ( A ) DESCRIPTION: /desc = "oligonucleotide for PCR"

( i i i ) HYPOTHETICAL: NO

( i v ) ANTI-SENSE: NO

( x i ) SEQUENCE DESCRIPTION: SEQ ID NO:1:

GAGTTGACTT TGAGGTTTCG C                                            2 1

( 2 ) INFORMATION FOR SEQ ID NO:2:

```
( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "reverse oligonucleotide
              primer for PCR"

( i i i ) HYPOTHETICAL: NO ( i v ) ANTI-SENSE: YES ( x i ) SEQUENCE DESCRIPTION: SEQ ID NO:2:

G C C C G T C T G T    C T T A T A G T G G                                    2 0
```

We claim:

1. A method of inducing 15-lipoxygenase in animal or human cells comprising monocytes, the method comprising administering an inducing amount of Interleukin-13 (IL-13) to said cells.

2. The method of claim 1 wherein the IL-13 is of the same species as the cells.

3. The method of claim 1 wherein human IL-13 is administered to human cells.

4. The method of claim 3 wherein IL-13 is administered to said cells in vivo.

5. The method of claim 3 wherein IL-13 is administered to said cells ex vivo.

6. The method of claim 3 wherein IL-13 is administered to said cells in vivo at a daily dose range of 10 ng/kg body weight to 1 mg/kg body weight.

7. A method of treating an inflammatory condition responsive to compounds whose biosynthesis involves 15-LO activity, comprising administering a 15-LO inducing amount of IL-13 to an animal or human with the inflammatory condition.

8. The method of claim 7 wherein compounds whose biosynthesis involves 15-LO activity are selected from the group consisting of 15-S-HETE or a lipoxin.

9. The method of claim 7 wherein a 15-LO inducing amount of IL-13 is a daily dose in the range 10 ng/kg body weight to 1 mg/kg body weight.

10. A method of treating an animal or human having an inflammatory condition mediated by monocyte/macrophage activity, comprising administering an effective amount of IL-13 to said animal or human.

11. The method of claim 10 wherein an effective amount of IL-13 is a daily dose in the range 10 ng/kg body weight to 1 mg/kg body weight.

12. A method of repressing 5-LO or $LTA_4$ hydroxylase in animal or human cells comprising monocytes, the method comprising the step of administering a repressing amount of IL-13 to said cells.

13. The method of claim 12 wherein the IL-13 is of the same species as the cells.

14. The method of claim 12 wherein human IL-13 is administered to human cells.

15. The method of claim 12 wherein IL-13 is administered to said cells in vivo.

16. The method of claim 12 wherein IL-13 is administered to said cells ex vivo.

17. A method of treating glomerulonephritis in an animal or human comprising administering a 15-LO inducing amount of IL-13 to said animal or human.

18. The method of claim 17 wherein an effective amount of IL-13 is a daily dose in the range 10 ng/kg body weight to 1 mg/kg body weight.

19. The method of claim 17 wherein the IL-13 is of the same species as the animal or human.

* * * * *

UNITED STATES PATENT AND TRADEMARK OFFICE
CERTIFICATE OF CORRECTION

PATENT NO. : 5,830,453

DATED : November 3, 1998

INVENTOR(S) : Badr et al.

It is certified that error appears in the above-identified patent and that said Letters Patent is hereby corrected as shown below:

In the Abstract, line 6, replace "15-s-hydroxyeicoiatetraenoic" with --15-s-hydroxyeicosatetraenoic--.
In column 8, lines 38-39, replace "90:3735143739" with --90:3735-3739--.

Signed and Sealed this

Thirtieth Day of March, 1999

*Attest:*

Q. TODD DICKINSON

*Attesting Officer*   Acting Commissioner of Patents and Trademarks